United States Patent [19]

Hardy

[11] 4,083,897
[45] Apr. 11, 1978

[54] PROCESS FOR PREPARING N-ALKYLATED AMINOALKYLPHOSPHONATES

[75] Inventor: Thomas A. Hardy, Monroe, N.Y.

[73] Assignee: Stauffer Chemical Company, Westport, Conn.

[21] Appl. No.: 740,585

[22] Filed: Nov. 10, 1976

[51] Int. Cl.$^2$ .............................................. C07F 9/40
[52] U.S. Cl. .................................. 260/970; 260/932; 260/945
[58] Field of Search .................. 260/970, 932, 945

[56] References Cited

U.S. PATENT DOCUMENTS

| 2,635,112 | 4/1953 | Fields | 260/970 |
| 2,870,190 | 1/1959 | Burgert et al. | 260/932 |
| 3,555,124 | 1/1971 | Beck et al. | 260/970 |

Primary Examiner—Richard L. Raymond
Attorney, Agent, or Firm—William R. Robinson

[57] ABSTRACT

N-Alkylated aminoalkylphosphonates having the structural formula:

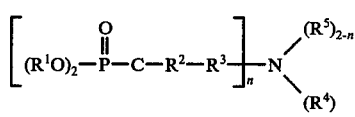

where $R^1$, $R^4$ and $R^5$ are straight or branched lower alkyl having one to five carbon atoms; $R^2$ and $R^3$ are selected from the group consisting of straight or branched lower alkyl having one to five carbon atoms and hydrogen and $n$ is the integer 1 or 2, are prepared with acid numbers from about 5 to about 15 by contacting an amine and a phosphite and then adding this to an aqueous solution of an aldehyde or ketone. The reaction temperature is kept below about 70° C. and water is removed under reduced pressure.

4 Claims, No Drawings

PROCESS FOR PREPARING N-ALKYLATED AMINOALKYLPHOSPHONATES

BACKGROUND OF THE INVENTION

1. Field of the Invention

The present invention relates, in general to a method of preparing N-alkylated aminoalkylphosphonates and particularly concerns an improved process for preparing such compounds with a low acid number.

2. The Prior Art

N-Alkylated aminoalkylphosphonates are well known and can be prepared by various techniques. Examples of these techniques are found in U.S. Pats. No. 3,268,450 and 3,555,124. These patents generally disclose the process:

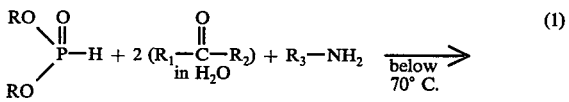  (1)

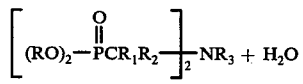

The water formed as a byproduct of this reaction is removed during the course of said reaction.

Other similar techniques wherein water is not removed until completion of the reaction are disclosed in U.S. Pat. Nos. 2,635,112; 2,847,442; 2,870,190; 3,076,010; 3,257,479; 3,314,957; 3,821,335 and 3,855,363.

Additionally, techniques wherein nonaqueous aldehyde or ketone is used in a similar reaction are disclosed in U.S. Pat. Nos.3,134,742; 3,257,479; 3,352,948; 3,385,914; 3,457,333; 3,498,969; 3,505,431 and 3,551,422. Products having a low acid number can be obtained by these techniques wherein nonaqueous aldehyde or ketone is used.

The present invention constititutes a significant improvement over the foregoing prior art. According to this invention, N-alkylated aminoalkylphosphonates having a low acid number can be made by utilizing aqueous aldehyde or ketone and by following the particular reaction procedure set forth in the present specification. It is desirable to obtain a low acid number product as this eliminates the need for a final and expensive distillation step. The procedure described has the advantage that nonaqueous aldehyde or ketone, which is undesirable to handle, does not have to be handled pursuant to the present invention.

SUMMARY OF THE INVENTION

In accordance with the present invention, N-alkylated aminoalkylphosphonates having an acid number of about 5 to about 15 milligrams of potassium hydroxide per gram of sample are prepared in good yields by following the sequence set forth below:

Step 1: A mixture of the appropriate amine and phosphite is prepared.

Step 2: The mixture of Step 1 is added to aqueous aldehyde or ketone.

Step 3: The reaction temperature is kept below about 70° C. and water is removed at the conclusion of the reaction.

The foregoing sequence has the advantage that hydrolysis is drastically reduced by first preparing the mixture of Step 1 prior to admixing with the aqueous aldehyde and ketone in Step 2. Step 3, of course, further enhances the low acid number of the product.

DETAILED DESCRIPTION OF THE INVENTION

The N-alkylated animoalkylphosphonates of the present invention have the structural formula:

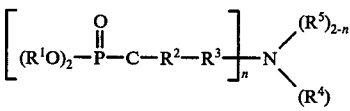  I where $R^1$, $R^4$ and $R^5$ are straight or branched lower alkyl having one to five carbon atoms; $R^2$ and $R^3$ are selected from the group consisting of straight or branched lower alkyl having one to five carbon atoms and hydrogen and $n$ is the integer one or two.

The reaction sequence according to the present invention is as follows:

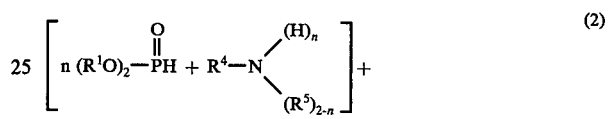  (2)

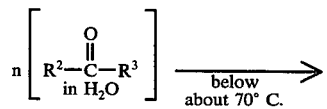

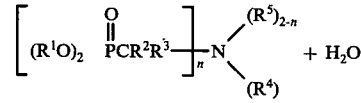

where $R^1$, $R^2$, $R^3$, $R^4$, $R^5$ and $n$ are as defined above.

The process of the present invention comprises mixing a phosphite having the formula:

  II wherein $R^1$ is as defined above, with an amine having the formula:

  III where $R^4$, $R^5$ and $n$ are as defined above. The reaction is then initiated by adding this mixture to an aqueous aldehyde or ketone having the formula:

  IV wherein $R^2$ and $R^3$ are as defined above. The reaction temperature is maintained below about 70° C. to minimize hydrolysis and is preferably maintained at about 55° C. to about 70° C. to minimize reaction time. Water is removed under reduced pressure after the reaction.

Reactants utilized in the process described above are generally employed in stoichiometric amounts. In this regard, it is critical to the present invention that no excess amine is present when the amine and phosphite are mixed. Otherwise, the phosphite will hydrolyze on mixture with water thereby forming acid.

Reaction times can vary over relatively wide ranges and can easily be determined by one skilled in the art. Temperature is the most important determinant of reaction time. Reaction time is decreased as reaction temperature is increased. As pointed out above, however, the reaction temperature should be maintained below about 70° C. to minimize hydrolysis.

The process of the present invention can be carried out continuously or batchwise utilizing conventional equipment.

The products of the present invention can be purified if desired, for example, by distillation or chromatography.

Identification of products can be achieved, for example, by infrared spectroscopy, nuclear magnetic resonance, boiling point determination and gas or liquid chromatography.

Typical product yields according to the present invention are from about 85% to about 99% of theoretrical.

Illustrative of the compounds corresponding to structural formula I are:

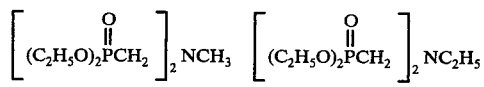

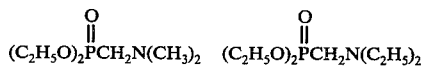

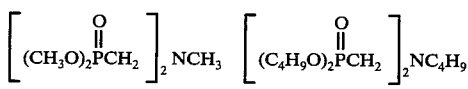

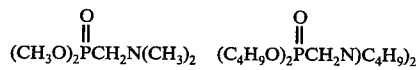

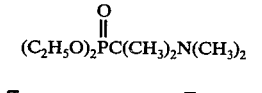

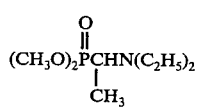

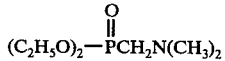

The products of the present invention are useful as flame retardants in plastics, urethanes and textiles and as lubricant additives having good corrosion inhibiting, anti-erosion and extreme pressure properties.

The present invention will be more fully illustrated in the examples which follow:

EXAMPLE I

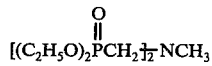

One mole of diethylphosphite was cooled to less than 0° C. and one mole of dimethylamine was then added. The solution was swirled and the mixture was then added to a jacketed, cooled (0° C.) addition funnel and added dropwise to 1.05 moles of formalin in a 250 ml flask. The temperature was kept below 30° C.

When the addition was complete, the solution was fully cooled to 5° C. for ½ hour. The pressure was then reduced to 5 mm Hg at 40° C. for one and one-half hours. The yield was 188 g (96% of theoretical) and the acid number was less than 5 mg KOH per gram of sample.

EXAMPLE II

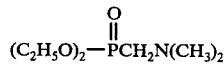

Two moles of diethylphosphite were cooled to −50° C. followed by the addition of one mole of methylamine. The solution was mixed and added to 2.1 moles of formalin by the same procedure as followed in Example 1. The reaction temperature was maintained between 25° and 28° C. during reaction. The product had an acid number of 4.8.

Water was then removed from the product at 1 mm Hg and less than 50° C. leaving the product with an acid number of 10.1. A portion of that material was then subjected to wipe filmed evaporation yielding a product with an acid number of 12.0

EXAMPLE III

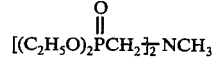

Two moles of diethylphospite were cooled to 0° C. and two moles of dimethylamine were then added slowly followed by mixing. The mixture was then added pursuant to the procedure of Example I to formalin. The reaction mixture was allowed to exotherm to 38°–40° C. during the addition over a period of 35 minutes. The solution was then allowed to exotherm at 38° C. for another 25 minutes after which the temperature began to drop. When the solution reached 35° C. it was transferred to a one liter flask. The flask was evaporated to 5 mm Hg at 40° C. for one hour. The acid number prior to removal of water was 7.6 and following removal of water was 11.2. The yield was 97% of theoretical.

EXAMPLE IV

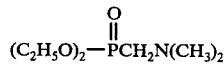

Two moles of diethylphosphite were cooled to minus 40° C. One mole of methylamine was then added and the solution was cooled and added to an addition funnel. The solution was then added dropwise to 2.1 moles of formaldehyde for one hour and ten minutes with the pot at 55° C. After the addition, the acid number of the solution was 5.4.

The pot was then cooled to 52° C. over 15 minutes and water was then removed for one hour at 50° C. and 5 mm Hg. The product was then stored in a refrigerator overnight and the next day the acid number was 8.1 with a water concentration of 1.1%.

What is claimed is:

1. A method of preparing N-alkylated aminolalkyl-phosphonates having the formula:

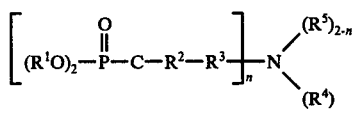

where $R^1$, $R^4$ and $R^5$ are the same or different and are selected from the group consisting of straight and branched lower alkyl having 1 to 5 carbons; $R^2$ and $R^3$ are the same or different and are selected from the group consisting of straight and branched lower alkyl having 1 to 5 carbons and hydrogen; and $n$ is the integer 1 or 2, comprising first preparing a mixture of a phosphite having the formula:

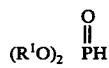

where $R^1$ is as defined above, with a stoichiometric amount of an amine having the formula:

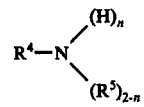

where $R^4$, $R^5$ and $n$ are as defined above, followed by adding said mixture to an aqueous reactant having the formula:

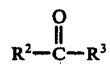

where $R^2$ and $R^3$ are as defined above, while maintaining the reaction temperature below about 70° C., followed by removal of water at the conclusion of the reaction.

2. The method of claim 1 wherein the reaction temperature is maintained from about 0° C. to below about 70° C.

3. The method of claim 1 wherein $R^1$ is ethyl, $R^4$ and $R^5$ are methyl and $n$ is 1.

4. The method of claim 1 wherein $R^1$ is ethyl, $R^4$ is methyl and $n$ is 2.